US010456287B2

(12) United States Patent
Shaffer

(10) Patent No.: US 10,456,287 B2
(45) Date of Patent: Oct. 29, 2019

(54) THERAPEUTIC SOCK

(71) Applicant: David Shaffer, Great Neck, NY (US)

(72) Inventor: David Shaffer, Great Neck, NY (US)

( * ) Notice: Subject to any disclaimer, the term of this patent is extended or adjusted under 35 U.S.C. 154(b) by 0 days.

(21) Appl. No.: 16/021,209

(22) Filed: Jun. 28, 2018

(65) Prior Publication Data

US 2019/0167462 A1 Jun. 6, 2019

Related U.S. Application Data

(60) Provisional application No. 62/595,175, filed on Dec. 6, 2017.

(51) Int. Cl.
*A61F 5/00* (2006.01)
*A61F 5/01* (2006.01)
*A41B 11/00* (2006.01)

(52) U.S. Cl.
CPC ............ *A61F 5/019* (2013.01); *A41B 11/003* (2013.01); *A41B 11/004* (2013.01); *A61F 5/0111* (2013.01); *A61F 5/0127* (2013.01); *A41B 2500/10* (2013.01)

(58) Field of Classification Search
CPC ...... A61F 13/064; A61F 13/068; A61F 5/019; A61F 13/06; A41B 11/004; A41B 11/003; A41B 11/02
See application file for complete search history.

(56) References Cited

U.S. PATENT DOCUMENTS

| 4,856,505 A | 8/1989 | Shaffer et al. | |
|---|---|---|---|
| 6,708,348 B1* | 3/2004 | Romay | D04B 1/26 2/239 |
| 8,663,178 B2* | 3/2014 | De Luca | A61F 5/019 2/239 |
| 2006/0247566 A1 | 11/2006 | Gobet et al. | |
| 2010/0106110 A1* | 4/2010 | De Luca | A61F 5/019 604/293 |
| 2010/0212068 A9* | 8/2010 | Nemcik | A41B 11/004 2/239 |
| 2011/0061664 A1 | 3/2011 | Paris Mayans Carlos | |

(Continued)

FOREIGN PATENT DOCUMENTS

| DE | 101 54 185 A1 | 5/2003 | |
|---|---|---|---|
| DE | 202015007262 U1 * | 12/2015 | ........... A41B 11/004 |
| WO | WO-2014019540 A1 * | 2/2014 | ........... A61F 5/0111 |

OTHER PUBLICATIONS

International Search Report and the Written Opinion of the International Searching Authority in PCT/US18/60913, dated Jan. 24, 2019.

*Primary Examiner* — Kim M Lewis
(74) *Attorney, Agent, or Firm* — Collard & Roe, P.C.

(57) ABSTRACT

A therapeutic sock is formed from a knit sock body formed in a tubular shape and terminating in a closed toe portion, the toe portion being divided into a first compartment configured accommodating a big toe and at least one additional compartment for other toes. At least one of the compartments has a area of increased compression as compared to a compression in other areas of the sock. The area of increased compression can be disposed on the first compartment and extend longitudinally along a medial edge of the first compartment and/or can be disposed on the at least one additional compartment and extend laterally around a circumference of the at least one additional compartment.

4 Claims, 3 Drawing Sheets

(56) References Cited

U.S. PATENT DOCUMENTS

| | | | |
|---|---|---|---|
| 2011/0088145 A1* | 4/2011 | Harada | A61F 5/0111 |
| | | | 2/240 |
| 2011/0119807 A1 | 5/2011 | Dellacorte et al. | |
| 2013/0060182 A1* | 3/2013 | Kotkamaa | A61F 5/019 |
| | | | 602/30 |
| 2014/0200494 A1* | 7/2014 | Winkler, Sr. | A61F 13/08 |
| | | | 601/84 |
| 2016/0309793 A1* | 10/2016 | Noh | A41B 11/004 |
| 2017/0007465 A1* | 1/2017 | Edwards | A61F 13/068 |
| 2017/0265527 A1* | 9/2017 | Kim | A41B 11/003 |
| 2017/0325513 A1* | 11/2017 | Jeong | A41B 11/003 |

* cited by examiner

THERAPEUTIC SOCK

CROSS-REFERENCE TO RELATED APPLICATIONS

This application claims priority under 35 USC 119(e) of U.S. Provisional Application Ser. No. 62/595,175, filed on Dec. 6, 2017, the disclosure of which is herein incorporated by reference.

BACKGROUND OF THE INVENTION

1. Field of the Invention

The present invention relates to a sock that helps to treat various foot conditions. In particular, the invention relates to a knitted sock having increased compression with or without therapeutic materials or threads in selected areas of the sock for treating specific foot conditions.

2. The Prior Art

Bunions form when the balance of forces around the first Metatarsal/Phalangeal joint of the big toe (Hallux) become disrupted. This can lead to foot instability. Abnormal functioning of the foot can lead to abnormal pressure being exerted within the foot. People who have low arches (flat feet) are prone to developing bunions and hammer toes due to poor biomechanics. A bunion can also cause the big toe to be pushed toward the second toe, causing the second toe to either overlap or underlap the Hallux. People with flat feet and/or excessive pronation can be predisposed to developing a bunion. As the foot flattens out, it becomes more unstable. As the middle of the foot loosens, the area along the side of the foot where the big toe sits becomes more mobile and pushes upward and rotates inward.

Hammer toes are the most common deformity of the second, third and fourth toes. A hammer toe is a toe that has an abnormal bend at the proximal interphalangeal joint, causing the toe to bend downward. Hammer toes can be quite painful and form from an imbalance in the surrounding muscles, tendons and ligaments that normally keep the toes straight. Without proper treatment, Hammer toes can progressively worsen, resulting in fixed deformities.

Hammer toes can be caused by improper footwear. For example, high heels or tight shoes can force the toes into a flexed position. Women are more likely than men to develop hammer toes, and the risk of developing hammer toes increases with age. In addition, people with arthritis and diabetes are more likely to develop hammer toes. The symptoms of a hammer toe are as follows: pain while wearing shoes, corns and callouses, swelling, redness, burning, an inability to straighten the toe.

There have been many attempts to provide relief to people suffering from these conditions. Toe loops and bandages are often used to secure toes to the adjacent toe, holding it in place, in an attempt to treat hammer toe deformities. However, this can cause irritation. Crest pads/gelpads/foam pads are used to treat hammer toes and bunions, but these are all in direct contact against the skin and can also cause irritation.

U.S. Pat. No. 4,856,505 discloses a sock having a restraining member for the big toe. The restraining member is a rigid attachment that forces the big toe into a straighter alignment, which reduces the pain an discomfort associated with the bunion.

While this device may be effective for treating bunions, it does not address the treatment of hammer toes that is commonly seen with bunion deformities.

SUMMARY OF THE INVENTION

It is therefore an object of the invention to provide a way to treat bunions and hammer toes that is comfortable, inexpensive and easy to use, and can be worn with most types of footwear, or as a stand-alone device, i.e, night splint or post-op splint.

This object is accomplished by a therapeutic sock formed of a tubular knit material with a closed, toe portion that is split into a compartment for the big toe, and a compartment for the remaining toes. The split-toe sock has been designed for treating a variety of medical conditions and deformities including hallux valgus (bunions), hallux malleus, hammer toes, flat feet, muscle fatigue, swelling/edema, plantar fasciitis along with heel and ankle pain. A band of increased compression is located along the medial aspect of the 1st compartment, extending proximately along the medial aspect of the big toe and forefoot. This area of increased compression pulls the big toe outward, aiding in the realignment of the big toe, and at the same time allow the big toe to separate from the other digits, which can alleviate the pain and discomfort from a bunion. The area of increased compression can be formed by a tighter knitting of the fabric of the sock, so that the sock exerts a compressive force against the portion of the foot that is contacted by the area of increased compression. The increased compression band on the big toe and foot exerts a force on the metatarsal/phalangeal joint, thus reducing mobility around the joint and decreasing the progression of bunion growth.

The second compartment is for the remaining toes. The second compartment also has a band of increased compression extending across the compartment, and preferably around the entire circumference of the compartment, for the purpose of controlling hammer toe deformities by putting compression pressure on both the extensor and flexor tendons of the toes.

The sock can also have an area of increased compression extending around the forefoot arch, as well as at the heel and ankle. The increased pressure of the sock in the arch area will help reduce pain in those individuals with plantar fasciitis, and also help those individuals with painful flatfeet by helping to reduce muscle fatigue and strain by pulling up on the plantar fascia, and relieving tension on muscles, tendons and ligaments.

Also, there is a correlation between flat feet and HAV deformity, so the additional compression around the arch may help reduce or slow down the progression of bunions by diminishing pronatory forces and creating a more stable foot. The increased compression and pressure in the arch, heel, and ankle will also reduce swelling and edema, and at the same time control the rear foot and ankle, to help reduce ankle strains and sprains and helping heel spurs.

The sock is made of a knitted material such as cotton, spandex/lycra, nylon and/or polyester. The sock can also have an area that utilizes a different material for therapeutic purposes. For example, an area along the outside of the first compartment can be knit with a combination of far-infrared thermoreactive materials/bio-ceramic threads or copper threads or other threads such as bamboo, as these have therapeutic value. For example, socks incorporating copper can stimulate the production of capillaries, collagen and key proteins that promote healthier and softer skin. Copper also helps to fight odor due to its antibacterial and anti-fungal properties. Threads impregnated with thermoreactive ceramic powder can be used to relieve pain, increase circulation by increasing blood flow and increasing oxygen levels of the tissues, decrease swelling in the feet, decrease cold feet and numbness and treat ankle sprains. These threads contain thermoreactive materials that convert heat into far-infrared rays, which are light rays having a wavelength between visible an microwave. Far-infrared waves can be used to relieve joint and tissue pain by increasing circulation and oxygen levels in the tissues. The band around the arch can also contain these threads, and these threads could be incorporated into other areas of the sock as well, such as the toes, bunion area, forefoot, mid-foot, rear foot, ankle and leg.

To increase the surface area of compression, the sock could also be configured with a separate compartment for each toe, so that there is an increased beneficial effect to the patient by increasing blood circulation, relieving inflammation, speeding up wound healing and decreasing the pain of arthritis. The area of increased compression can be disposed around the entire circumference of each toe. Unlike conventional socks, where the toes are in limited contact with the sock (touching only the top and bottom surfaces of the toes), the therapeutic sock with its individual compartments increases the sock-to-toe surface contact (top, bottom and sides). This increase in surface area around the toe allows therapeutic fibers to be absorbed on the skin in a more efficient and uniform manner. Concurrently, an increase in compression (around the toe) will help straighten out, realign and hold the toes in place, creating a more stable environment.

This split-toe sock can be made on sock machine or a glove machine, or by any other conventional method. Using a flat knitting machine such as a glove machine reduces thickness and in some cases eliminates irritating seams and makes the sock more comfortable and less irritating in and out of footwear. The areas of increased compression can be formed by knitting the sock material in a different, tighter pattern in a band along the outside of the big toe, and around the second compartment, as well as in the band around the arch and/or around the ankle and heel, so that the sock fits tighter in the areas of increased elastic compression than in the rest of the sock. Alternatively, different threads could be incorporated into the sock that increase the density or tightness of the band so that the band exerts a compressive force on the area of the foot or toe that it contacts.

The sock can be worn day or night and used as a splint, and can also be used as a post-operative device to keep surgical corrections in alignment. The sock can also be used to prevent bunions and hammer toes in people who are prone to developing them and in those people who do not want surgery and/or are not surgical candidates.

BRIEF DESCRIPTION OF THE DRAWINGS

Other objects and features of the present invention will become apparent from the following detailed description considered in connection with the accompanying drawings. It is to be understood, however, that the drawings are designed as an illustration only and not as a definition of the limits of the invention.

In the drawings, wherein similar reference characters denote similar elements throughout the several views.

DETAILED DESCRIPTION OF THE PREFERRED EMBODIMENTS

Figure 1:
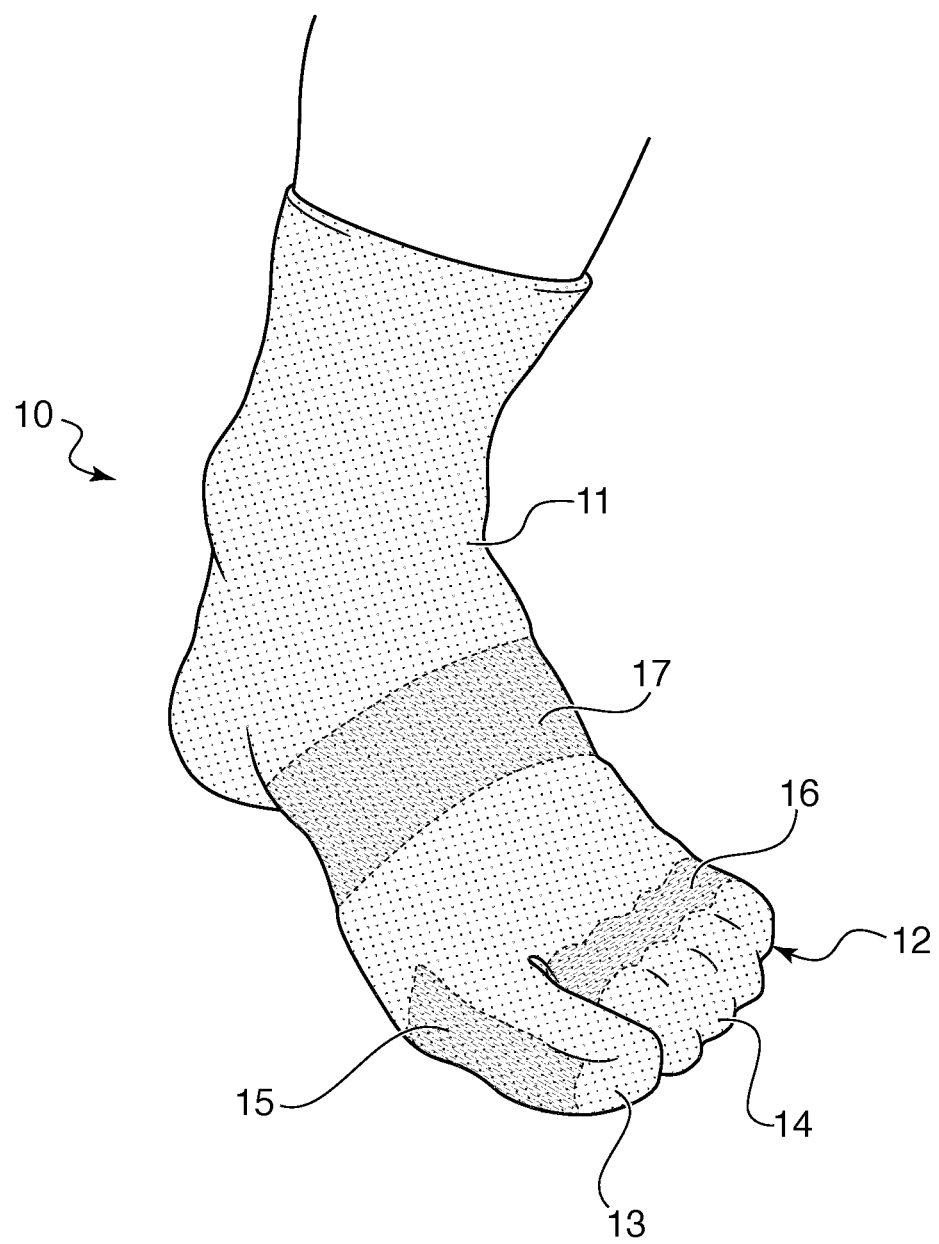
FIG. 1 shows one embodiment of the therapeutic sock according to the invention.
Figure 2:
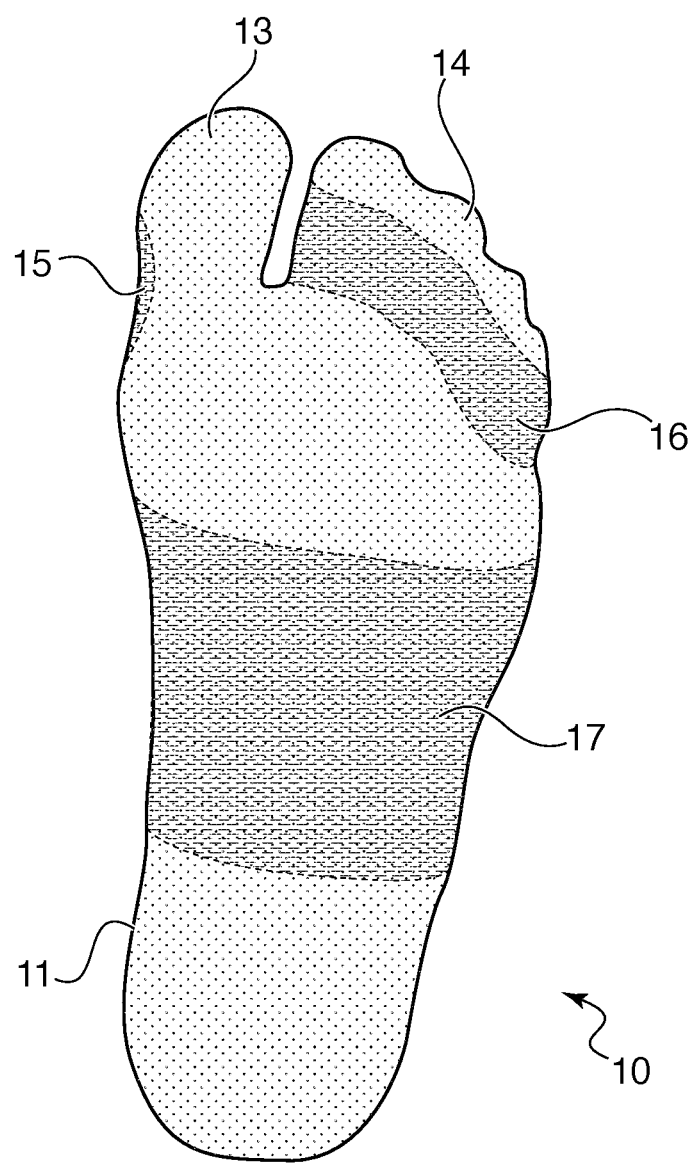
FIG. 2 shows a bottom view of the sock in another variation.

Referring now in detail to the drawings and, in particular, FIGS. 1 and 2 show a therapeutic sock 10 according to one embodiment of the invention. Sock 10 is formed of a tubular knit sock body 11 that terminates in a closed toe portion 12. Toe portion 12 is separated into a first compartment 13 for accommodating a big toe, and a second compartment 14, for accommodating the four remaining toes.

An area of increased compression 15 is disposed along the medial aspect of the big toe and foot on the surface of sock 10, in the region of first compartment 13. This area of increased compression 15 can be formed by knitting the sock threads in a different, tighter, pattern to increase the elastic compressive force on the toe, or by incorporating different threads into the area, so that the area 15 exerts a force on the big toe inside of compartment 13 and pulls the toe away from the lesser toes. A second area of increased compression 16 can be disposed laterally around the second compartment 14. This area 16 can also be formed via a tighter knitting pattern or by incorporating additional or different types of threads into the knit fabric. The band of increased compression around the second compartment helps in treating hammer toes, as it forces the toes to straighten by applying pressure on the flexor and extensor tendons of the toes, causing the toes to straighten out and thus limiting the pressure and rubbing of the hammer toes in footwear.

In addition, a band of increased compression 17 can be disposed around the arch portion of the therapeutic sock 10. This band helps to treat flat feet and over-pronation by supporting the arch of the foot. This band 17 could also be formed by a tighter or different knitting pattern or by incorporating threads of different materials or elasticity.

Figure 3:
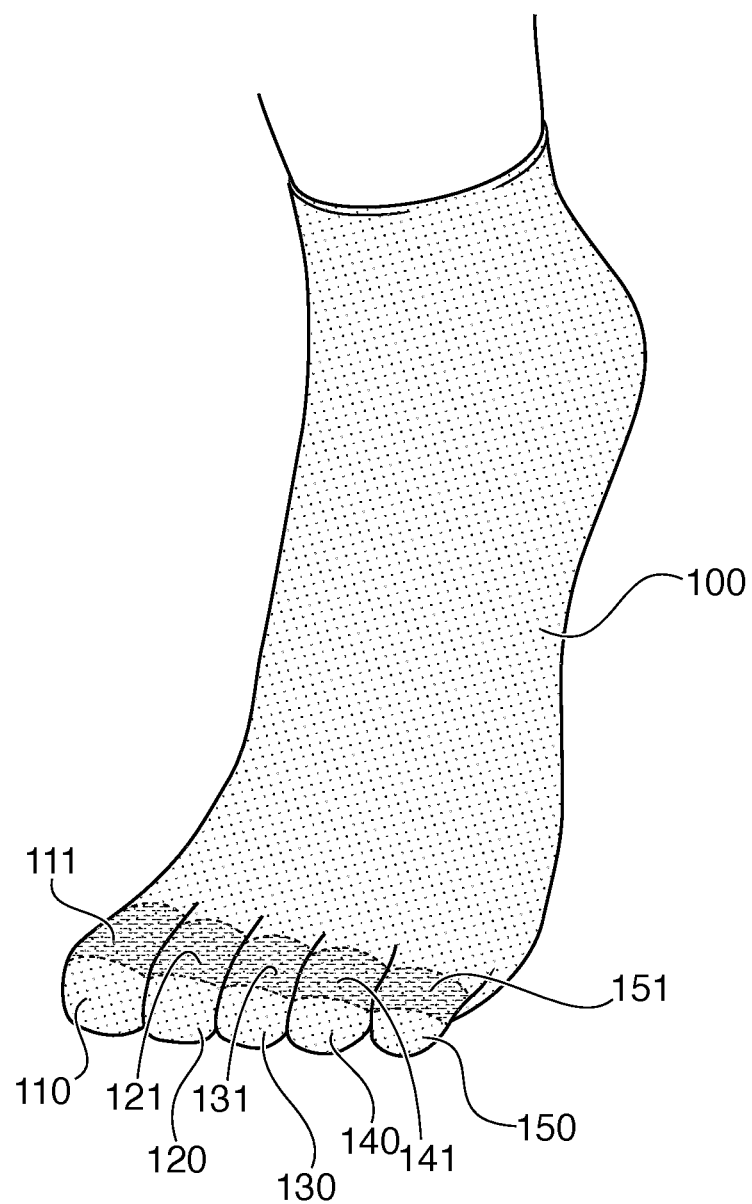
FIG. 3 shows another embodiment of the sock according to the invention.

Another embodiment of the sock according to the invention is shown in FIG. 3. Here, sock 100 has a toe section that is formed of five separate compartments: a big toe compartment 110, and four separate toe compartments 120, 130, 140 and 150 for the other four toes. A band of increased compression is disposed around each of the five compartments, as shown by bands 111, 121, 131, 141 and 151. These bands can be formed around the entire circumference of each of the toe compartments. The increased surface area afforded by the individual toe compartments allows for greater compression on each toe, to press the toes into better alignment and avoid the pain and discomfort from hammer toes. A side strip of extra compression can also be provided along the outside of the big toe, as with area 15 in FIGS. 1 and 2, to provide better support and guidance for a bunion as well.

Accordingly, while only a few embodiments of the present invention have been shown and described, it is obvious that many changes and modifications may be made thereunto without departing from the spirit and scope of the invention.

What is claimed is:
1. A therapeutic sock comprising;
a sock body formed in a tubular shape and terminating in a closed toe portion, the toe portion being divided into a first compartment configured to accommodate a big toe and four additional compartments for other toes, wherein the sock is formed from a knit material, and wherein each of the four additional compartments has an area of increased compression as compared to a compression in other areas of the sock, the area of increased compression having threads formed of a different material than a material of the rest of the sock, wherein the area of increased compression extends laterally around a circumference of each of the additional compartments and extends only around a proximal portion of the additional compartments to such a length that the area of increased compression provides compression pressure on extensor and flexor tendons of the toes, wherein a distal portion of the additional compartments does not have an area of increased compression, wherein the threads formed of different material contain a material selected from the group consisting of copper and ceramic powder, and wherein there is an additional area of increased compression extending longitudinally along a medial edge of the sock, in a region of the first compartment.

2. The therapeutic sock according to claim 1, wherein the area of increased compression is formed by a knitting pattern that differs from a knitting pattern in other areas of the sock.

3. The therapeutic sock according to claim 1, further comprising an area of increased compression in an area remote from the toe portion, for increasing compression on an arch of the foot when the therapeutic sock is worn by an individual.

4. The therapeutic sock according to claim 3, wherein the area of increased compression in the area remote from the toe portion extends around an entire circumference of the sock.

* * * * *